(12) United States Patent
Shah et al.

(10) Patent No.: US 9,492,111 B2
(45) Date of Patent: Nov. 15, 2016

(54) METHODS AND MATERIALS FOR STABILIZING ANALYTE SENSORS

(75) Inventors: Rajiv Shah, Rancho Palos Verdes, CA (US); Udo Hoss, Sherman Oaks, CA (US); Gopikrishnan Soundararajan, North Hills, CA (US); Nannette M. Van Antwerp, Valencia, CA (US); Barry Pham, Los Angeles, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 2259 days.

(21) Appl. No.: 11/493,054

(22) Filed: Jul. 26, 2006
(Under 37 CFR 1.47)

(65) Prior Publication Data

US 2008/0027287 A1    Jan. 31, 2008

(51) Int. Cl.
  *A61B 5/00*       (2006.01)
  *A61B 5/1486*     (2006.01)
  *A61B 5/145*      (2006.01)

(52) U.S. Cl.
  CPC ....... *A61B 5/14865* (2013.01); *A61B 5/14532* (2013.01); *A61B 5/6849* (2013.01)

(58) Field of Classification Search
  CPC ............ A61B 5/14532; A61B 5/14865; A61B 5/1486
  USPC ........................................ 600/345, 347, 365
  See application file for complete search history.

(56) References Cited

U.S. PATENT DOCUMENTS

| | | |
|---|---|---|
| 2,402,950 A | 7/1946 | Culver et al. |
| 2,519,541 A | 8/1950 | Bryant |
| 2,899,658 A | 8/1959 | Bean, Jr. |
| 4,034,959 A | 7/1977 | Morrison |
| 4,104,099 A | 8/1978 | Scherrer |
| 4,163,544 A | 8/1979 | Fowler et al. |
| 4,356,074 A | 10/1982 | Johnson |

(Continued)

FOREIGN PATENT DOCUMENTS

| | | |
|---|---|---|
| EP | 0 747 069 A2 | 12/1996 |
| EP | 0 826 382 A2 | 3/1998 |

(Continued)

OTHER PUBLICATIONS

Flexible circuits at Extreme Density, 8 unnumbered pages of various dates (Metrigraphics, Wilmington, MA).

(Continued)

*Primary Examiner* — Christian Jang
(74) *Attorney, Agent, or Firm* — Gates & Cooper LLP

(57) ABSTRACT

The disclosure provides a sensor including a sensor having an external surface and a cannula. The cannula comprises a substantially cylindrical wall encircling a lumen, at least one aperture and a distal end. The sensor is positioned within the lumen and the distal end of the cannula extends beyond the sensor. This configuration functions for example to stabilize chemical reactions associated with the sensor by creating a buffer zone between the sensor and the surrounding tissues at the site of implantation. In certain embodiments, the sensor can further comprise an accessory material in proximity to the external surface, wherein the accessory material modifies the biological response of a tissue that is in contact with the sensor. The sensor can also comprise anchors that keeps the sensor in contact with subcutaneous tissue of a subject upon insertion of the sensor into the body of the subject.

22 Claims, 3 Drawing Sheets

(56) References Cited

U.S. PATENT DOCUMENTS

| | | |
|---|---|---|
| 4,373,009 A | 2/1983 | Winn |
| 4,373,527 A | 2/1983 | Fischell |
| 4,560,375 A | 12/1985 | Schulte et al. |
| 4,568,250 A | 2/1986 | Falk et al. |
| 4,569,641 A | 2/1986 | Falk et al. |
| 4,573,994 A | 3/1986 | Fischell et al. |
| 4,626,244 A | 12/1986 | Reinicke |
| 4,636,150 A | 1/1987 | Falk et al. |
| 4,654,006 A | 3/1987 | Kusano et al. |
| 4,714,234 A | 12/1987 | Falk et al. |
| 4,759,828 A | 7/1988 | Young et al. |
| 4,769,013 A | 9/1988 | Lorenz et al. |
| 4,783,441 A | 11/1988 | Thurow |
| 4,890,620 A | 1/1990 | Gough |
| 4,897,173 A | 1/1990 | Nankai et al. |
| 4,950,256 A | 8/1990 | Luther et al. |
| 4,958,661 A | 9/1990 | Holtermann et al. |
| 5,001,009 A | 3/1991 | Whitbourne |
| 5,019,260 A | 5/1991 | Gsell et al. |
| 5,077,210 A | 12/1991 | Eigler et al. |
| 5,108,819 A | 4/1992 | Heller et al. |
| 5,128,170 A | 7/1992 | Matsuda et al. |
| 5,165,407 A | 11/1992 | Wilson et al. |
| 5,178,366 A | 1/1993 | Kojima et al. |
| 5,183,472 A | 2/1993 | Jaehrling et al. |
| 5,196,088 A | 3/1993 | Soda |
| 5,200,051 A | 4/1993 | Cozzette et al. |
| 5,212,050 A | 5/1993 | Mier et al. |
| 5,229,172 A | 7/1993 | Cahalan et al. |
| 5,281,324 A | 1/1994 | Kiesele et al. |
| 5,288,636 A | 2/1994 | Pollmann et al. |
| 5,299,571 A * | 4/1994 | Mastrototaro ............... 600/347 |
| 5,322,063 A | 6/1994 | Allen et al. |
| 5,328,954 A | 7/1994 | Sarangapani |
| 5,330,911 A | 7/1994 | Hubbell et al. |
| 5,331,027 A | 7/1994 | Whitbourne |
| 5,390,671 A | 2/1995 | Lord et al. |
| 5,390,691 A | 2/1995 | Sproule |
| 5,391,250 A | 2/1995 | Cheney, II et al. |
| 5,411,647 A | 5/1995 | Johnson et al. |
| 5,415,938 A | 5/1995 | Cahalan et al. |
| 5,433,710 A | 7/1995 | Van Antwerp et al. |
| 5,482,473 A | 1/1996 | Lord et al. |
| 5,568,806 A | 10/1996 | Cheney, II et al. |
| 5,607,475 A | 3/1997 | Cahalan et al. |
| 5,609,629 A | 3/1997 | Fearnot et al. |
| 5,620,738 A | 4/1997 | Fan et al. |
| 5,643,681 A | 7/1997 | Voorhees et al. |
| 5,648,442 A | 7/1997 | Bowers et al. |
| 5,662,960 A | 9/1997 | Hostettler et al. |
| 5,672,638 A | 9/1997 | Verhoeven et al. |
| 5,702,754 A | 12/1997 | Zhong |
| 5,702,818 A | 12/1997 | Cahalan et al. |
| 5,711,959 A | 1/1998 | Kohler et al. |
| 5,777,060 A | 7/1998 | Van Antwerp |
| 5,786,439 A | 7/1998 | Van Antwerp et al. |
| 5,804,048 A | 9/1998 | Wong et al. |
| 5,809,242 A | 9/1998 | Shaw et al. |
| 5,858,186 A | 1/1999 | Glass |
| 5,913,040 A | 6/1999 | Rakavy et al. |
| 5,914,026 A * | 6/1999 | Blubaugh et al. ............ 600/347 |
| 5,939,208 A | 8/1999 | Stoy |
| 5,964,993 A | 10/1999 | Blubaugh, Jr. et al. |
| 6,011,537 A | 1/2000 | Slotznick |
| 6,013,855 A | 1/2000 | McPherson et al. |
| 6,103,033 A | 8/2000 | Say et al. |
| 6,162,611 A | 12/2000 | Heller et al. |
| 6,336,904 B1 * | 1/2002 | Nikolchev .................... 600/562 |
| 6,340,421 B1 | 1/2002 | Vachon et al. |
| 6,368,274 B1 | 4/2002 | Van Antwerp et al. |
| 6,411,998 B1 | 6/2002 | Bryant et al. |
| 6,413,393 B1 | 7/2002 | Van Antwerp et al. |
| 6,497,729 B1 | 12/2002 | Moussy et al. |
| 6,551,276 B1 | 4/2003 | Mann et al. |
| 6,558,351 B1 | 5/2003 | Steil et al. |
| 7,153,265 B2 | 12/2006 | Vachon |
| 7,813,780 B2 | 10/2010 | Shah et al. |
| 2002/0023852 A1 * | 2/2002 | Mcivor et al. ................ 206/305 |
| 2002/0031532 A1 * | 3/2002 | Uchiyama ..................... 424/401 |
| 2003/0032874 A1 * | 2/2003 | Rhodes et al. ................ 600/347 |
| 2003/0100040 A1 | 5/2003 | Bonnecaze et al. |
| 2004/0008956 A1 | 1/2004 | Frohne et al. |
| 2004/0009161 A1 | 1/2004 | Escary |
| 2004/0074785 A1 | 4/2004 | Holker et al. |
| 2006/0020189 A1 | 1/2006 | Brister et al. |
| 2006/0079740 A1 | 4/2006 | Silver et al. |
| 2007/0227907 A1 | 10/2007 | Shah et al. |

FOREIGN PATENT DOCUMENTS

| | | |
|---|---|---|
| JP | 60173452 | 9/1985 |
| WO | 91/15993 A1 | 10/1991 |
| WO | WO 98/07458 | 2/1998 |
| WO | WO 98/08553 | 3/1998 |
| WO | WO 98/10805 | 3/1998 |
| WO | WO 98/19627 | 5/1998 |
| WO | WO 98/56293 | 12/1998 |
| WO | WO 99/21703 | 5/1999 |
| WO | WO 99/22993 | 5/1999 |
| WO | WO 99/45375 | 9/1999 |
| WO | WO 99/45387 | 9/1999 |
| WO | WO 99/56613 | 11/1999 |
| WO | WO 01/58348 | 8/2001 |
| WO | 2006/017358 | 2/2006 |
| WO | 2006/029293 A1 | 3/2006 |

OTHER PUBLICATIONS

Kimura, J. et al., 1989, "Evaluation of an Albumin-Based, Spin-Coated, Enzyme-Immobilized Membrane for an Isfet Glucose Sensor by Computer Simulation," Journal of Membrane Science, 43:291-305.

Koudelka, M., et al., "Planar Amperometric Enzyme-Based Glucose Microelectrode", Sensors and Actuators, 18 (Elsevier Sequoia, The Netherlands—1989), pp. 157-165.

Koudelka, M., et al., "In-vivo Behaviour of Hypodermically Implanted Microfabricated Glucose Sensors", *Biosensors & Bioelectronics 6*, (Elsevier Science Publishers Ltd., England—1991) pp. 31-36.

Mastrototaro, John J., et al., "An electroenzymatic glucose sensor fabricated on a flexible substrate", *Sensors and Actuators B.5* (Elsevier Sequoia 1991), p. 139-144.

"Metrigraphics Ion Beam Etching Capability", 1 page, no date (Metrigraphics, Wilmington, MA).

"3M Specifications and Design Guidelines, Microflex Circuits for IC Interconnect Solutions," pp. 1-32 (the entire document), 1997 (3M Electronic Products Division, Austin, TX).

"3M Offers More Solutions for the Semiconductor Industry", the entire document, 1997 (3M Electronic Products Division, Austin, TX).

"Microflex Solutions from 3M", the entire document, 1996 (3M Electronic Products Division, Austin, TX).

"5 Micron Wide Conductors and Spaces on . . . PZT, Alumina, Glass and Flexible Materials", 1 page, no date (Metrigraphics, Wilmington, MA).

Thurow et al., "Stabilisation of Dissolved Proteins Against Denaturation at Hydrophobic Interfaces," Diabetologia, 1984, 27: 212-218.

Urban, G., et al., "Miniaturized multi-enzyme biosensors integrated with pH sensors on flexible polymer carriers for in vivo applications", *Biosensors & Bioelectronics* 7 (Elsevier Science Publishers Ltd.—1992) pp. 733-739.

Wilke, D. et al., 1992, "Application of Redox Mediators in Enzyme Electrodes," Proc. Conf. Trends Electrochem. Biosens., pp. 155-161.

Yao, T., 1983, Analytica Chim. Acta, 148:27-33.

Japanese Office Action dated May 8, 2012 for Japanese application No. 2009-521831.

(56) References Cited

OTHER PUBLICATIONS

European Office Action dated Apr. 13, 2010, Application No. 07810797.6.
PCT International Search Report and Written Opinion dated Mar. 6, 2008, PCT Application No. PCT/US2007/016785.

* cited by examiner

METHODS AND MATERIALS FOR STABILIZING ANALYTE SENSORS

CROSS REFERENCE TO RELATED APPLICATIONS

This application is related to commonly owned U.S. patent application Ser. No. 10/127,745, filed Apr. 22, 2002, Ser. No. 11/301,512, filed Dec. 13, 2005 and Ser. No. 11/397,543, filed Apr. 4, 2006, the entire contents of each of which are incorporated herein by reference.

TECHNICAL FIELD OF THE INVENTION

This invention relates generally to the manufacture and use of sensor systems suitable for subcutaneous implantation, intravenous use, and other placements involving direct contact between the sensor and the tissue or fluid to be sampled. Such sensor systems are capable of improved performance and stability and a reduction in background noise.

BACKGROUND OF THE INVENTION

Biomedical sensors, such as those that utilize enzyme electrodes, can be used to determine the concentrations of a wide variety of analytes and the like rapidly and with considerable accuracy. For example, glucose sensors having enzyme electrodes suitable for in vivo use are typically prepared by depositing a glucose sensitive enzyme, such as glucose oxidase, onto an electrode via an electromotive plating process. Sensors having enzyme electrodes are used, for example, to detect a number of well known analytes such as glucose, urea, uric acid, various alcohols, and a number of amino acids.

Biomedical sensor configurations currently in use typically require a minimum of one polymeric membrane at the interface with the in vivo environment. This membrane which interacts with the in vivo environment in which the sensor is placed can serve a number functions. For example, such membranes can function to limit diffusion, e.g. of glucose, while maintaining high oxygen permeability. In addition, such membranes can function to provide a biocompatible interface with the surrounding tissue.

The introduction of a foreign material such as a sensor into the body, however, typically results in protein deposition or fouling at the surface of the material or device. In particular, following the deposition of protein at the surface, a new surface is essentially created. This new surface influences the temporal sequence of events associated with the healing process. In the context of a sensor, shortly after the injury initiated by implantation of the sensor, cells such as monocytes arrive at the material surface and can differentiate into macrophages soon thereafter. Macrophages are potent generators of damaging chemicals that aid in the process of phagocytosis. These chemical entities and by-products can include hydroxyl radical, superoxide, and strong acids, which may diffuse through the membrane to the underlying enzyme layer. The accumulation of bodies and reagents at the boundary between the sensor and the material to be sampled can introduce noise and interfere with sensor performance.

SUMMARY OF THE INVENTION

The invention disclosed herein has a number of embodiments. Typical embodiments include a sensor system designed to reduce noise and/or enhance sensor performance and stability, typically by creating a buffer zone (i.e. a protected zone where alterations in chemical reaction conditions are inhibited and/or minimized) at the 3-D interface where the analyte reacts with the sensor. One illustrative embodiment is a sensor system comprising a sensor having a chemically reactive surface that reacts with an analyte to be sensed; and a cannula comprising a substantially cylindrical housing that surrounds the sensor; at least one aperture disposed in the housing that allows the analyte to diffuse therethrough so as to contact the chemically reactive surface; and an end that extends beyond an end of the sensor.

Such sensor systems can be used in a variety of methods designed to enhance sensor function, for example long term sensor performance. Another embodiment of the invention is a method of stabilizing an environment for a chemical reaction between an in vivo analyte and an enzyme that reacts with the analyte, the method comprising performing the chemical reaction using an implanted sensor system comprising a sensor having a chemically reactive surface comprising the enzyme; and a cannula comprising a substantially cylindrical housing that encircles the sensor; at least one aperture disposed in the housing that allows the analyte to diffuse therethrough so as to contact the chemically reactive surface; and an end that extends beyond an end of the sensor, wherein the aperture and the chemically reactive surface of the implanted sensor system form a stabilized chemical reaction environment that is further stabilized by the end of the cannula that extends beyond an end of the sensor, so that the environment for the chemical reaction between the in vivo analyte and the enzyme that reacts with the analyte is stabilized.

The methods that utilize the sensor systems of the invention are useful in a variety of contexts. For example, the methods can be used so that the environment of the chemical reaction is stabilized so as to inhibit fluctuations in the ratio between the signal generated by the analyte and signal noise not generated by the analyte. Alternatively, the methods can be used so that the environment of the chemical reaction is stabilized so as to inhibit fluctuations in the ratio between the signal generated by the analyte and signal noise not generated by the analyte that results from movement of the sensor at the site of implantation. Alternatively, the methods can be used so that the environment of the chemical reaction is stabilized so as to inhibit fluctuations in the ratio between the signal generated by the analyte and signal noise not generated by the analyte that results from the accumulation of in vivo materials at the site of implantation. Alternatively, the methods can be used so that the environment of the chemical reaction is stabilized so as to inhibit fluctuations in the ratio between the signal generated by the analyte and signal noise not generated by the analyte that results from a localized depletion of a reactant the site of implantation.

As discussed in detail below, the sensor systems of the invention can incorporate a variety of additional elements, for example an anchor that couples the system to the site of implantation and inhibits movement of the sensor or an accessory material provided in proximity to the chemically reactive surface, wherein the accessory material modifies the biological response of a tissue that is in contact with the sensor system (e.g. protein deposition, inflammation or proliferation of macrophages or foreign body giant cells). Such modifier materials include hydrophilic polymers, anti-inflammatory agents including steroids such as dexamethasone or clot inhibiting agents. Typically, the coating is coupled to the cannula of the system (e.g. the cannula housing). Optionally, the accessory material is provided in proximity to the chemically reactive surface, and for example is disposed in the aperture such that the surface of the accessory material is substantially flush with the surface of the cannula.

The invention also provides additional articles of manufacture including sensor elements, sensor systems and kits. In one such embodiment of the invention, a kit and/or sensor system or set, useful for the sensing an analyte as is described above, is provided. The kit and/or sensor system typically comprises a container, a label and a sensor as described above. The typical embodiment is a kit comprising a container and, within the container, an analyte sensor system having a design as disclosed herein and instructions for using this analyte sensor apparatus.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

DETAILED DESCRIPTION

Figure 1:
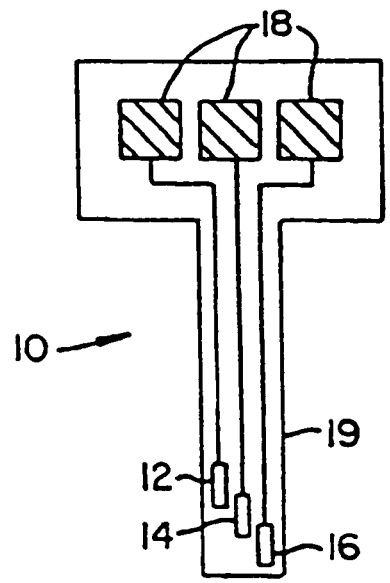
FIG. 1A is a schematic top view of a sensor 10 comprising an electrode 14 in accordance with the present invention.
FIG. 1B is a sectional side view of a working electrode 14 prepared in accordance with the present invention.
Figure 1:
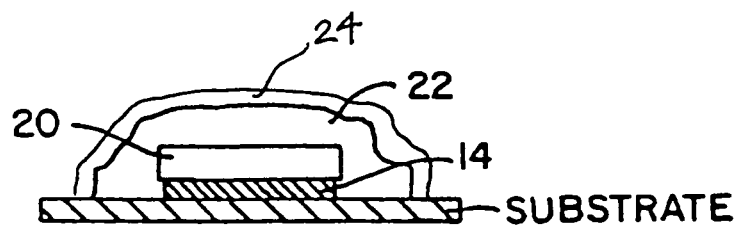

Embodiments of the invention described herein are based on the discovery that the performance of a sensor, such as a sensor implanted in biological tissue, can be improved by providing a buffer zone around the sensor at the interface with the tissue or fluid to be sampled. Without being bound by a specific scientific theory, it is believed that the buffer zone generated by the sensor systems recited herein stabilizes the reaction conditions by inhibiting alterations in the reaction conditions at the 3-D interface where the analyte reacts with the sensor. Such a buffer zone can be created by placing the sensor inside a tube or cannula, wherein the cannula extends beyond the length of the sensor. One or more apertures in the cannula provide access to the sensor. The configuration of the sensor can be further modified to enhance sensor performance and to adapt the sensor for a particular use.

All scientific and technical terms used in this application have meanings commonly used in the art unless otherwise specified. As used in this application, the following words or phrases have the meanings specified.

As used herein, "modifying the biological response of a tissue" means altering a biological response that occurs in tissue upon introduction of a foreign object, such as an implanted sensor. Examples of such biological responses include protein biofouling or deposition, inflammation, macrophage and/or foreign body giant cell invasion and/or cellular proliferation. Typically, the modifying includes inhibiting or minimizing undesirable biological responses that reduce or impede sensor performance. The modifying can occur by a variety of means, including chemical, biological and structural. For example, a chemical modification could include reducing inflammation, a biological modification could include inhibiting cell proliferation, and a structural modification could include preventing a giant cell invasion from contacting an implanted sensor.

As used herein, "hydrophilic polymer" means a polymer having a strong tendency to bind or absorb water, which is sufficient to result in swelling and formation of gels. This property is characteristic of some natural polymers, including carbohydrates, proteins and man-made polymers (e.g., hydrogels).

As used herein, "affixed to" means attached to, stuck to or fused with such that a substance affixed to a surface remains substantially attached to or closely associated with the surface.

As used herein, "provided in proximity to" means that a substance or material is affixed to, or positioned alongside, another substance or material sufficiently close so that molecules released by one substance or material will influence the chemical and biological environment of the other substance or material. Typically, in the context of a fiber serving as an accessory material to a sensor, the fiber can be provided in proximity to the sensor by co-implantation of the fiber and the sensor, whereby the two materials may or may not be in physical contact along some or all of their lengths, yet molecules released by the fiber will influence the biological response of the tissue into which the sensor has been implanted.

As used herein, "a" or "an" means at least one, and unless clearly indicated otherwise, includes a plurality.

Overview

Embodiments of the invention provide a sensor having one or more configurations or modifications that reduce noise and/or enhance sensor performance and stability by creating a buffer zone (i.e. a protected zone where alterations in the reaction conditions are inhibited and/or minimized) at the 3-D interface where the analyte reacts with the sensor. Improved sensors of the invention provide a buffer zone between the sensor surface and the tissue environment to be sampled to minimize interfering movements and/or agents or depletion of reactants. Optionally, a coating or accessory material is provided in proximity to the sensor. The invention additionally provides sensors having anchoring structures that prevent unwanted sensor displacement from the site of implantation. Methods that use the sensor systems of the invention to accomplish one or more advantageous goals (e.g. to reduce signal to noise rations) are also provided.

Typical Sensor System Embodiments of the Invention

FIG. 1 illustrates an exemplary sensor 10 including a working electrode 14 plated with an enzyme. As shown in FIG. 1A, a sensor 10 can have a reference electrode 12, a working electrode 14, and a counter electrode 16 deposited on a polymeric sheet 19. The sensor 10 further includes a series of bonding pads 18. FIG. 1B shows a cross-sectional view of the working electrode 14 covered with a layer 20 of an enzyme, such as glucose oxidase. The entire electrode array can then be coated with a layer 22 of a polymer. The electrodes can be made of any conductive surface, e.g., gold, platinum, palladium, chromium, copper, aluminum, pyrolitic carbon, composite material (e.g., metal-polymer blend), nickel, zinc, titanium, or an alloy, such as cobalt-nickel-chromium, or titanium-aluminum-vanadium, which is deposited on any of a variety of suitable materials, including glass, polyimide or polyester. In some embodiments, the electrode array includes a flex-circuit layout/design. Of course, those skilled in the art will recognize that variations of the above components, and other types of electrodes can be used in the method of the invention. The sensor 10 is coated further with a hydrophilic polymer 24, which provides for reduction of biofouling and enhanced sensor performance in a biological environment.

Figure 2A:
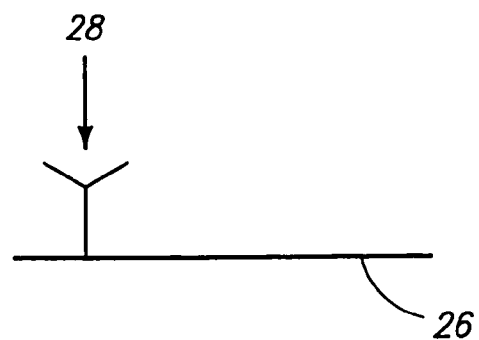
FIG. 2A is a schematic side view of an optical affinity sensor 26 without a coating, showing a representative glucose binding site 28.
Figure 2B:
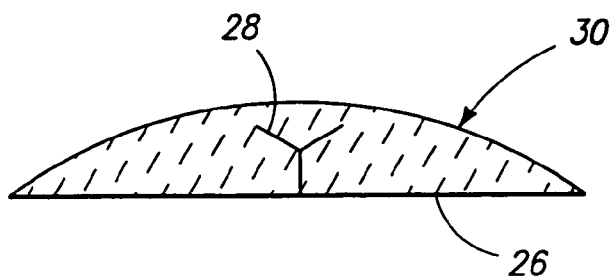
FIG. 2B is a schematic side view of an optical sensor 26 as shown in FIG. 2A, but with a coating 30.

In some embodiments, the sensor is an optical affinity sensor. FIG. 2A is a schematic side view of an optical affinity sensor 26 without a coating, showing a representative glucose binding site 28. The sensor 26, which includes a reflective substrate, can be coated with a hydrophilic, biocompatible and glucose permeable coating 26, as shown schematically in FIG. 2B. Optical sensors for detection of analytes are described in U.S. Pat. Nos. 6,256,522, and 5,143,066.

Other examples of sensors are described in U.S. Pat. No. 4,671,288 (electrochemical sensor); U.S. Pat. No. 5,320,725 (amperometric sensor); U.S. Pat. No. 5,403,700 (polyimide-based sensor design); and U.S. Pat. No. 5,540,828 (sensor with a polymer-modified surface). Those skilled in the art can readily appreciate the ability to adapt the teachings of the present invention to a variety of known sensor types and configurations.

The invention disclosed herein has a number of embodiments. Embodiments of the invention include a sensor system constructed to include a material that inhibits motion disturbances that can compromise the fidelity of the sensor. Embodiments of the invention also provide sensors constructed to include a material that inhibits in vivo biological responses that can compromise the fidelity of the sensor. One such embodiment is a sensor having an external surface, and a cannula. The cannula typically comprises a substantially cylindrical wall that creates a tube or lumen-like space in which the sensor is adapted to fit, at least one aperture and a distal end. The sensor is positioned within the lumen and the distal end of the cannula extends beyond an end of the sensor. This configuration protects the sensor by creating a buffer zone at the interface between the sensor and the surrounding tissues at the site of implantation. The sensors of the invention can be, for example, an enzymatic, molecular recognition, optochemical or electrochemical sensor. A typical sensor of the invention is a glucose sensor. A related embodiment of the invention is a sensor system comprising a sensor having chemically reactive surface that react with an analyte to be sensed; and a cannula comprising a substantially cylindrical housing that surrounds the sensor; at least one aperture disposed in the housing that allows the analyte to diffuse therethrough so as to contact the chemically reactive surface; and an end that extends beyond an end of the sensor.

In some embodiments of the invention, the sensor system comprises one or more accessory materials provided in proximity to the external surface, wherein the accessory material modifies the biological response of a tissue that is in contact with the sensor. The biological response typically comprises protein deposition, inflammation or proliferation of macrophages or foreign body giant cells. The accessory material can alter the biological response or alter the extent to which the sensor is in contact with the tissue affected by the biological response. The accessory material can be a coating affixed to the cannula. The coating can be affixed to the lumen of the cannula, for example. In one embodiment, the accessory material coats the surface of the portions of the sensor that are exposed to the in vivo environment, for example, by eliminating depressions where fluids can potentially accumulate and stagnate. The accessory material may fill at least one aperture, or up to all apertures in a multiple-aperture configuration of the cannula. In addition, or alternatively, the accessory material comprises a hydrophilic polymer. Examples of hydrophilic polymers include, but are not limited to, polyhydroxyethylmethacrylate (PHEMA), polyurethane, polysaccharide, polyacrylamide, or polyurea. In one embodiment, the hydrophilic polymer comprises polyethylene oxide (PEO). Representative PEOs include, but are not limited to, polyurethane, polyurea and cross-linked PEO. In certain embodiments of the invention, the coating comprises a biologically active substance such as dexamethasone or another biological response modifier. In some embodiments, the accessory material comprises a sustained release material that delivers a therapeutic agent. The therapeutic agent can be, for example, an anti-inflammatory, anti-bacterial, anti-viral, anti-coagulant, anti-proliferative or disinfecting agent, or a growth factor. The invention additionally provides a method for delivering a biologically active substance to a subject using a sensor of the invention. The method comprises implanting a sensor of the invention into a tissue of the subject. The accessory material comprises the biologically active substance.

In certain embodiments of the invention, the sensor system further comprises one or more anchors that keep the sensor in contact with subcutaneous tissue of a subject upon insertion of the sensor into the body of the subject. The anchor can comprise barbs affixed to the cannula, or one or more coils affixed to the cannula. In some embodiments, the anchor expands after insertion of the sensor into the body of the subject.

A related embodiment of the invention is a method of stabilizing an environment for a chemical reaction between an in vivo analyte and an enzyme that reacts with the analyte. The term "stabilizing" as in "stabilizing an environment for a chemical reaction" is used in accordance with its art-accepted meaning of working to keep the reaction conditions under which the chemical reaction occurs relatively unchanged. In particular, as it is known that chemical reactions are influenced by environmental factors such as pH, temperature, relative concentrations of the reactants (e.g. stoichiometry) etc. In situations where a chemical reaction is used to obtain data over a period of time (e.g. in an implanted electrochemical glucose sensor), it is desirable to create a stable reaction environment so that the data and information generated by the chemical reactions are not confounded by fluctuations in the reaction conditions. In this context, embodiments of the invention include a method of stabilizing an environment for a chemical reaction between an in vivo analyte and an enzyme that reacts with the analyte, the method comprising performing the chemical reaction using an implanted sensor system comprising a sensor having a chemically reactive surface comprising the enzyme; a cannula comprising a substantially cylindrical housing that encircles the sensor; at least one aperture disposed in the housing that allows the analyte to diffuse therethrough so as to contact the chemically reactive surface; and an end that extends beyond an end of the sensor, wherein the aperture and the chemically reactive surface of the implanted sensor system form a stabilized chemical reaction environment that is further stabilized by the end of the cannula that extends beyond an end of the sensor, so that the environment for the chemical reaction between the in vivo analyte and the enzyme that reacts with the analyte is stabilized.

Without being bound by a specific scientific theory, it is believed that the sensor systems recited herein stabilize the reaction conditions by creating a buffer zone at the 3-D interface where the analyte reacts with the sensor, for example, at a sensor electrode coated with an enzyme that reacts with the analyte (e.g. glucose analyte reacting with an electrode coated with glucose oxidase). In certain embodiments of the invention, the system functions to inhibit fluctuations (e.g. a decrease) in the ratio between the signal generated by the analyte and signal noise not generated by the analyte. For example, certain embodiments of the system where the cannula end extends beyond an end of the sensor can inhibit the motion that can cause a reactive surface of the sensor to move and possibly expose the reactive surface to microenvironments having different reaction conditions, thereby altering the analyte signal and or the noise. In related embodiments, the system can inhibit the accumulation of materials (e.g. proteins and cells) on the sensor that can expose the reactive surface to microenvironments having different reaction conditions, thereby altering the analyte signal and or the noise. In certain embodiments of the invention, the aperture structure that permits an analyte to diffuse therethrough so as to contact the chemically reactive surface can further stabilize the reaction conditions by further sheltering the reaction components from exposure to fluctuating microenvironments having different reaction conditions that further alter the analyte signal and/or the noise. In related embodiments, the aperture is filled with an accessory material that permits diffusion therethrough, while further sheltering the reaction components from exposure to fluctuating microenvironments. Optionally, the accessory material is an agent that can modify a biological response to the implantation, for example an anti-inflammatory or anti-clotting agent. Certain embodiments of the implanted sensor system used in the method further comprise additional stabilizing elements, for example an anchor that couples the system to the site of implantation and further inhibits movement of the sensor. The combination of these specific elements serves to stabilize the reaction conditions, thereby providing benefits to the sensor such as more consistent and/or accurate reading over time.

As noted above, in certain embodiments, the implanted sensor system used in the method further comprises an accessory material provided in proximity to the chemically reactive surface, wherein the accessory material modifies the biological response of a tissue that is in contact with the sensor system. Such embodiments can further stabilize the reaction conditions by inhibiting the accumulation of materials at the site of implantation that can alter the reaction conditions. Optionally, the accessory material is disposed in the aperture such that the surface of the accessory material is substantially flush with the surface of the cannula. In this context, a related embodiment is a method of delivering a biologically active substance to a subject comprising implanting a sensor system described herein into a tissue of the subject, wherein the accessory material comprises the biologically active substance.

Typical Cannula Embodiments of the Invention

The cannula comprises a substantially cylindrical wall encircling a lumen, at least one aperture and a distal end. The sensor is positioned within the lumen and the distal end of the cannula extends beyond the sensor. This configuration protects the sensor by creating a buffer zone at the interface between the sensor and the surrounding tissues at the site of implantation. In one embodiment, the cannula comprises polyurethane. In a typical embodiment of the invention, a cannula having one or more apertures is produced using conventional methods, including obtaining a pre-formed cannula and modifying the cannula to provide appropriate apertures. Alternatively, the open end of a cannula can serve as an aperture.

A sensor can be positioned within the lumen of the cannula such that the one or more apertures provide access to the sensor sufficient to permit detection of an analyte in the environment into which the sensor is introduced. The positioning of the sensor within the cannula further provides a buffer zone between the environment and the sensor.

Those skilled in the art will appreciate that the cannula need not be strictly cylindrical to achieve the objective of providing a protected housing for the sensor. For example, an elongated tube, not necessarily circular in cross-section, having an opening or cavity that runs the length of the tube (lumen) sufficient to enclose the sensor is encompassed within the meaning of substantially cylindrical.

Typical Accessory Materials for Use with Embodiments of the Invention

In some embodiments, the sensor further comprises an accessory material provided in proximity to the external surface wherein the accessory material modifies the biological response of a tissue that is in contact with the sensor and/or provides a barrier or filter between the sensor and surrounding tissue. Accordingly, the accessory material can alter the biological response or alter the extent to which the sensor is in contact with the tissue affected by the biological response. The accessory material can reduce interference of the biological response with sensor performance, for example, by reducing noise and/or preventing unwanted reagents from interfering with analyte detection. The biological response typically comprises protein deposition, inflammation or proliferation of macrophages or foreign body giant cells.

The accessory material can be a coating affixed to one or more surfaces of the cannula or the sensor. The coating can be affixed to the lumen of the cannula, for example. The accessory material can fill at least one aperture, or up to all apertures in a multiple-aperture configuration of the cannula. The coating can be designed to limit the diffusion of materials, thereby restricting the materials that make contact with the sensor.

In some embodiments, the accessory material includes a hydrophilic coating. The coating applied to a sensor embodiment of the invention includes a hydrophilic polymer. Examples of hydrophilic materials include, but are not limited to, polyureas, polyamides, polyurethanes, acrylates, polyesters, polyethylene oxide (PEO) or cross-linked PEO. A preferred hydrophilic material for use in accordance with the invention is a PEO containing polyurethane or PEO containing polyurea. PEOs can be cross-linked by a variety of methods known in the art, including via the use of a gas plasma, or ionizing radiation such as electron or gamma sources, for example.

It is desirable to obtain a very hydrophilic membrane at the interface between the sensor and the biological environment. Accordingly, the coating is at least sufficiently hydrophilic to achieve swelling and gel formation. Preferably, the coating is sufficiently hydrophilic that, upon contact with a wet environment, it achieves a swell volume of at least about two, three, four or five times the thickness of the coating in a dry environment. Preferably, the coating is sufficiently hydrophilic, oxygen permeable and/or optically transparent so as to not change the overall analyte sensing capability of the sensor. Ideally, the coating achieves the maximal swell volume that does not disrupt adhesion with the underlying material.

Preferred hydrophilic materials include, but are not limited to, PEO containing polyurethanes, such as HydroMed™ TPH-D640 (available from CardioTech International). Such a polyurethane is suitable for application over the top of polymeric coatings currently in use with glucose sensors, such as glucose limiting polymer (GLP; MiniMed, Inc., Northridge, Calif.). In such applications, the hydrophilic material preferably does not limit glucose and is readily incorporated into the sensor and/or cannula production process.

Preferably the hydrophilic material is applied to the sensor by spraying the coating onto the sensor surface, e.g., over the GLP or optochemical sensing polymer. The preferred polymer does not impede the diffusion of glucose, is soluble in a volatile organic solvent such as tetrahydrofuran (THF) or isopropyl alcohol or mixture thereof (e.g., 25/75) that is suitable for spraying without disrupting the original surface. Damage to the underlying surface could affect the mass transfer properties of the underlying material and result in erratic sensor behavior. Alternatively, the hydrophilic material can be applied to the sensor and/or cannula by painting, dipping or other means known in the art.

In one embodiment, the accessory material is modified to deliver a therapeutic agent. The accessory material of the sensor embodiment of the invention provides for improved biocompatibility by reducing biofouling and other undesirable effects of the biological response to an implanted device and also provides enhanced sensor performance. Further enhancement of sensor performance can be provided by including an anti-inflammatory agent in the accessory material. In one embodiment, the coating comprises dexamethasone or other biological response modifier.

Typical Fibers for Use with Embodiments of the Invention

In another embodiment, the accessory material comprises a fiber. Representative fiber materials include, but are not limited to, natural fibers such as cotton, polypropylene, polyurethane, polyester, degradable suture materials such as polylactic acid (PLA) and polyglycolic acid (PGA) and co-polymers of lactic acid and glycolic acid (PLGA), or other materials that can be formulated with a therapeutic agent. The fiber is preferably modified to deliver a therapeutic agent. The therapeutic agent can be integrated into the fiber during fiber production, or applied to an existing fiber as a coating.

Figure 3A:
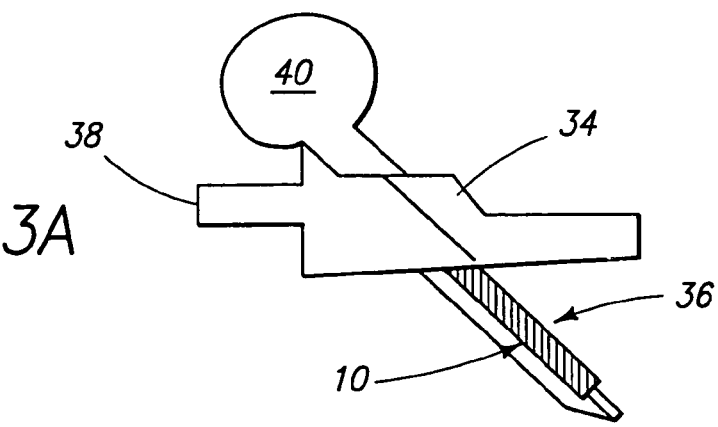
FIG. 3A is a schematic side view of a sensor 10 and fiber 32 inserted through the skin with the assistance of a connector 38 and a needle 36 that houses the sensor and filter.
Figure 3B:
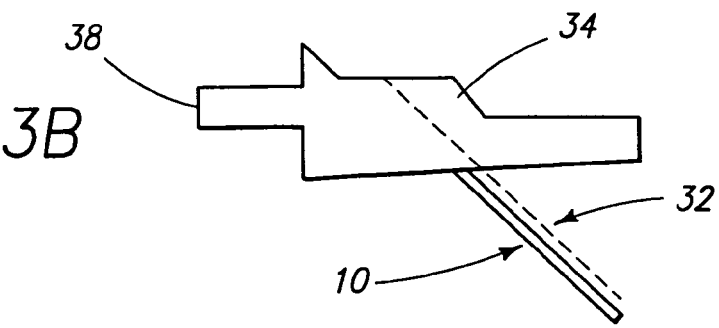
FIG. 3B is a schematic side view of the sensor 10 shown in FIG. 3A after removal of the needle 36, leaving the sensor 10 and fiber 32 in place.
Figure 4:
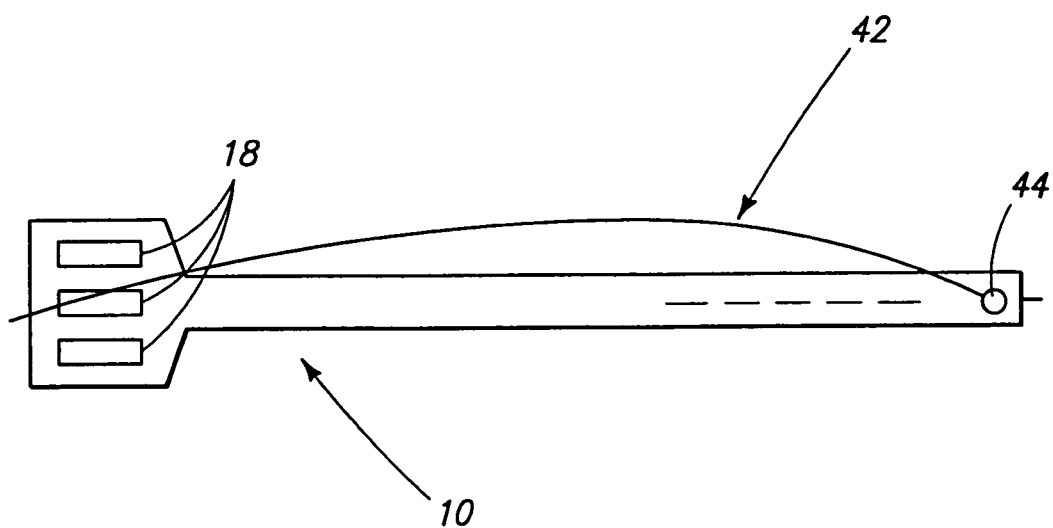
FIG. 4 is a schematic top view of a sensor with a fiber 42 that passes through a hole 44 at the distal end of the fiber and extends to the sensor 10 base.

The fiber 32 can be affixed to, or otherwise provided with, the sensor 10 (or cannula) in any of a variety of ways, as would be appreciated by those skilled in the art. For example, the fiber 32 can be attached to the sensor base 34 so that the fiber 32 can be easily removed together with the sensor 10. FIG. 3A is a schematic side view of a sensor 10 and fiber 32 inserted through the skin with the assistance of a connector 38 and a hollow needle 36 that houses the sensor 10 and fiber 32. FIG. 3B is a schematic side view of the sensor 10 shown in FIG. 3A after removal of the needle 36 via the removable insertion guide 40, leaving the sensor 10 and fiber 32 in place. FIG. 4 shows a schematic top view of a sensor 10 to which a fiber 32 has been affixed by passing the fiber 32 through a hole 42 at the distal end of the sensor 10. Alternatively, the fiber 32 can be affixed to the sensor 10 by inserting the fiber into a groove in the sensor 10, or by using an adhesive or other attachment means sufficient to keep the fiber 32 in close proximity to the sensor 10 upon placement in a biological environment. Affixing the fiber 32 to the distal end of the sensor 10 can facilitate keeping the fiber in position upon placement.

Those skilled in the art will appreciate other means by which a fiber can be provided in close proximity to the sensor, without necessarily affixing the fiber directly to the sensor. For example, the fiber can be co-inserted with the sensor at the time of implantation so that the fiber is positioned in close proximity to the sensor. Alternatively, the fiber can be affixed to the cannula and positioned to run through the lumen, placing it in proximity to the sensor.

Typical Therapeutic Agents for Use with Embodiments of the Invention

A medicinal or therapeutic agent can be incorporated into the hydrophilic material for the coating of the sensor or incorporation into the accessory material. The agent is selected in accordance with the desired effect. For example, the objective may be to prevent or minimize inflammation or microbial infection. Examples of therapeutic agents include, but are not limited to, anti-inflammatory, anti-bacterial, anti-viral, anti-coagulant, and disinfecting agents, such as dexamethasone, cefazolin, and benzalkonium chloride, and/or a growth factor. In some embodiments, the therapeutic agent may be an anti-proliferative agent that kills growing cells such as microbial organisms or reactive cells. In a preferred embodiment, the hydrophilic coating includes an anti-inflammatory agent, such as dexamethasone or a salt thereof. Suitable water-soluble salts of dexamethasone include, but are not limited to, the sodium phosphate or acetate salts. Dexamethasone serves to reduce inflammation and also to deactivate macrophages, which allows for enhanced sensor performance.

Typical Polymer Layers for Use with Embodiments of the Invention

In one embodiment, the polymer layer 22 comprises polyurea (see, e.g., U.S. Pat. Nos. 5,777,060 and 5,786,439). Examples of a suitable polymer layer for a sensor include, but are not limited to, glucose limiting polymer (GLP; Medtronic MiniMed, Inc., Northridge, Calif.). Other formulations of the polymer layer can be selected in accordance with the desired use. For example, U.S. Pat. Nos. 5,777,060 and 5,786,439 describe coatings suitable for use with sensors, particularly for use with glucose oxidase and glucose detection. These coatings share features in common with GLP, and can be adapted for use with other types of sensors.

Typical Anchors for Use with Embodiments of the Invention

In one embodiment, the sensor system further comprises an anchor that keeps the sensor in contact with subcutaneous tissue of a subject upon insertion of the sensor into the body of the subject. The anchor can prevent unwanted movement and/or withdrawal of the sensor from the site of implantation. The anchor can also facilitate obtaining and maintaining the sensor at a shallower depth than would otherwise be practical.

The anchor can comprise barbs or the like affixed to the cannula, or one or more coils or the like affixed to the cannula. In some embodiments, the anchor expands after insertion of the sensor into the body of the subject. In one embodiment, the anchor comprises a compressed, expanding coil. The coil can be introduced into the environment via a needle, for example, and then allowed to expand upon release from the insertion needle.

Suitable materials from which the anchor can be constructed include any one of the wide variety of biocompatible materials having appropriate material properties for anchoring (e.g. strength, elasticity and the like). Such materials include but are not limited to metals (including shape memory alloys) as well as polymeric materials such as plastics and the like. In one illustrative embodiment, the anchor comprises Nitinol.

Further Methodological Embodiments of the Invention

Embodiments of the invention additionally provide a method for producing a sensor system. In a typical embodiment of the invention, a cannula having one or more apertures/windows is produced using conventional methods, including obtaining a pre-formed cannula and modifying the cannula to provide appropriate apertures. Alternatively, the open end of a cannula can serve as a window. A sensor is further produced using conventional means, and positioned within the lumen of the cannula such that the one or more apertures provide access to the sensor sufficient to permit detection of an analyte in the environment into which the sensor system is introduced. The positioning of the sensor within the cannula further provides a buffer zone between the environment and the sensor. In another embodiment, the method of producing a sensor system comprises providing a sensor with anchor as described herein. The anchor can be affixed directly to the sensor or to a cannula in which the sensor is housed.

In one embodiment, the method includes coating a sensor system with a hydrophilic polymer. Preferably, the polymer is a PEO-containing polymer that is sprayed or painted onto the sensor as a lacquer. Those skilled in the art will appreciate a variety of manners by which the sensor can be coated and dried. In another embodiment, the method includes affixing a fiber to a sensor or cannula, or otherwise providing a fiber in close proximity to the external surface of the sensor. The fiber can be affixed to the sensor by attachment to the sensor and/or to the cannula, preferably at the sensor base and/or to a distal end of the sensor. The fiber can be affixed by adhesion to the sensor and/or cannula, and/or by mechanical means, such as by passing the fiber through a hole in the sensor/cannula or lodging the fiber into a groove in the sensor/cannula. Preferably, the coating or fiber is modified to deliver a therapeutic agent.

In addition, embodiments of the invention provide a method for monitoring or detecting a biological substance in a subject. The biological substance may be glucose, lactate, amino acids or other analyte of interest. The method includes contacting a sensor of the invention with a tissue or biological fluid, such as interstitial fluid or blood, of the subject, and detecting the presence of the substance or analyte via the sensor. The method provides more efficient and effective substance detection and monitoring because of reduced interference, inflammation and/or biofouling of the sensor. The method is particularly suited for subjects requiring repeated and/or continuous monitoring of an analyte, such as glucose for people with diabetes.

The invention additionally provides a method of delivering a biologically active substance to a subject comprising implanting a sensor of the invention into a tissue of the subject, wherein the accessory material comprises the biologically active substance. In a preferred embodiment, the biologically active substance comprises a cytokine, growth factor or therapeutic agent.

The foregoing description of preferred embodiments of the invention has been presented for the purposes of illustration and description. It is not intended to be exhaustive or to limit the invention to a precise form disclosed. Many modifications and variations are possible in light of the above teaching. It is intended that the scope of the invention be limited not by this detailed description, but rather by the claims appended hereto. Throughout this application various publications are referenced. The contents of each of these publications are incorporated herein by reference.

What is claimed is:

1. A sensor system comprising:
   a sensor having a chemically reactive surface that reacts with an analyte to be sensed; and
   a cannula comprising:
   a substantially cylindrical housing that surrounds the sensor;
   at least one aperture disposed in the housing that allows the analyte to diffuse therethrough so as to contact the chemically reactive surface;
   an end that extends beyond an end of the sensor;
   an accessory material provided in proximity to the chemically reactive surface, wherein:
   the accessory material fills the at least one aperture of the cannula;
   the accessory material is disposed in the aperture such that a surface of the accessory material is substantially flush with a surface of the cannula; and
   the sensor system is adapted to contact a tissue such that the accessory material is configured to contact and modify a biological response of the tissue.

2. The sensor system of claim 1, wherein the cannula comprises polyurethane.

3. The sensor system of claim 1, wherein the biological response comprises protein deposition, inflammation or proliferation of macrophages or foreign body giant cells.

4. The sensor system of claim 1, wherein the accessory material comprises a hydrophilic polymer.

5. The sensor system of claim 4, wherein the hydrophilic polymer comprises polyhydroxyethylmethacrylate (PHEMA), polyurethane, polysaccharide, polyacrylamide, or polyurea.

6. The sensor system of claim 4, further comprising an anchor that assists sensor contact with subcutaneous tissue of a subject upon insertion of the sensor into a subject.

7. The sensor system of claim 6, wherein the anchor comprises barbs affixed to the cannula.

8. The sensor system of claim 6, wherein the anchor expands after insertion of the sensor into the subject.

9. The sensor system of claim 1, wherein the sensor comprises an enzymatic, molecular recognition, optochemical or electrochemical sensor.

10. The sensor system of claim 1, wherein the sensor comprises a glucose sensor.

11. The sensor system of claim 1, wherein the accessory material comprises a sustained release material that delivers a therapeutic agent.

12. The sensor system of claim 11, wherein the therapeutic agent comprises an anti-inflammatory, anti-bacterial, anti-viral, anti-coagulant, anti-proliferative or disinfecting agent, or a growth factor.

13. A method of stabilizing an environment for a chemical reaction between an in vivo analyte and an enzyme that reacts with the analyte, the method comprising performing the chemical reaction using an implanted sensor system comprising:
a sensor having an chemically reactive surface comprising the enzyme; and
a cannula comprising:
a substantially cylindrical housing that encircles the sensor;
at least one aperture disposed in the housing that allows the analyte to diffuse therethrough so as to contact the chemically reactive surface; and
an end that extends beyond an end of the sensor,
wherein the aperture and the chemically reactive surface of the implanted sensor system form a stabilized chemical reaction environment that is further stabilized by the end of the cannula that extends beyond an end of the sensor, and
an accessory material provided in proximity to the chemically reactive surface, wherein:
the accessory material fills the at least one aperture of the cannula;
the accessory material is disposed in the aperture such that a surface of the accessory material is substantially flush with a surface of the cannula; and
the sensor system is adapted to contact a tissue such that the accessory material is configured to contact and modify a biological response of the tissue;
so that the environment for the chemical reaction between the in vivo analyte and the enzyme that reacts with the analyte is stabilized.

14. The method of claim 13, wherein the environment of the chemical reaction is stabilized so as to inhibit fluctuations in the ratio between a signal generated by the analyte and signal noise not generated by the analyte.

15. The method of claim 13, wherein the environment of the chemical reaction is stabilized so as to inhibit fluctuations in the ratio between a signal generated by the analyte and signal noise not generated by the analyte that results from the accumulation of in vivo materials at the at a site of implantation.

16. The method of claim 13, wherein the implanted sensor system used in the method further comprises an anchor that couples the system to a site of implantation and inhibits movement of the sensor.

17. The method of claim 13, wherein the accessory material comprises a hydrophilic polymer, an anti-inflammatory agent or a clot inhibiting agent.

18. The method of claim 13, wherein the accessory material comprises a hydrophilic polymer.

19. The method of claim 18, wherein the hydrophilic polymer comprises polyhydroxyethylmethacrylate (PHEMA), polyurethane, polysaccharide, polyacrylamide, or polyurea.

20. A method of delivering a biologically active substance to a subject comprising implanting a sensor system into a tissue of the subject comprising:
a sensor having chemically reactive surface that reacts with an analyte to be sensed;
an accessory material provided in proximity to the chemically reactive surface,
a cannula comprising:
a substantially cylindrical housing that surrounds the sensor;
at least one aperture disposed in the housing that allows the analyte to diffuse therethrough so as to contact the chemically reactive surface, wherein:
the accessory material fills the at least one aperture of the cannula;
the accessory material is disposed in the aperture such that a surface of the accessory material is substantially flush with a surface of the cannula; and
the sensor system is adapted to contact a tissue such that the accessory material is configured to contact and modify a biological response of the tissue; and
an end that extends beyond an end of the sensor,
wherein the accessory material comprises the biologically active substance.

21. The method of claim 20, wherein the accessory material comprises a hydrophilic polymer.

22. The method of claim 21, wherein the hydrophilic polymer comprises polyhydroxyethylmethacrylate (PHEMA), polyurethane, polysaccharide, polyacrylamide, or polyurea.

* * * * *